(12) United States Patent
Müller et al.

(10) Patent No.: US 8,097,240 B2
(45) Date of Patent: Jan. 17, 2012

(54) USE OF TRANSMISSION DYES FOR PROTECTING HUMAN SKIN FROM BROWNING AND AGEING

(75) Inventors: Stefan Müller, Weil am Rhein (DE); Jürg Haase, Bettingen (CH); Thomas Ehlis, Freiburg (DE); Gilbert Kreyer, Saint-Louis (FR); Jochen Giesinger, Grenzach-Wyhlen (DE); Martin Vogt, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 598 days.

(21) Appl. No.: 12/086,648

(22) PCT Filed: Dec. 11, 2006

(86) PCT No.: PCT/EP2006/069519
§ 371 (c)(1),
(2), (4) Date: Jan. 13, 2009

(87) PCT Pub. No.: WO2007/071584
PCT Pub. Date: Jun. 28, 2007

(65) Prior Publication Data
US 2009/0214453 A1    Aug. 27, 2009

(30) Foreign Application Priority Data

Dec. 21, 2005  (EP) .................................. 05112636
May 24, 2006  (EP) .................................. 06114467

(51) Int. Cl.
*A61Q 17/04* (2006.01)
*C07D 241/04* (2006.01)

(52) U.S. Cl. .......................................... 424/60; 544/387
(58) Field of Classification Search .................. None
See application file for complete search history.

(56) References Cited

U.S. PATENT DOCUMENTS

2005/0201957 A1    9/2005  Richard .......................... 424/59

FOREIGN PATENT DOCUMENTS

| | | |
|---|---|---|
| EP | 1407757 | 4/2004 |
| EP | 1484051 | 12/2004 |
| FR | 2842419 | 1/2004 |
| GB | 2412866 | 10/2005 |
| JP | 62138423 | 6/1987 |
| WO | 01/18125 | 3/2001 |
| WO | 02/03940 | 1/2002 |
| WO | 02/092041 | 11/2002 |
| WO | 2004/043412 | 5/2004 |
| WO | 2004/052837 | 6/2004 |
| WO | 2007/007283 | 1/2007 |

OTHER PUBLICATIONS

English language abstract of EP 1484051, Dec. 8, 2004.
English language abstract of JP 62138423, Jun. 22, 1987.
Anonymous: "Amino substituted hydroxyphenyl benzophenone derivatives", IP.com Journal, Aug. 4, 2003.

*Primary Examiner* — Tracy Vivlemore
*Assistant Examiner* — Jennifer Berrios
(74) *Attorney, Agent, or Firm* — Shiela A. Loggins

(57) ABSTRACT

Disclosed is the use of an aqueous dispersion comprising (a) a micronized sparingly soluble organic compound which has a UV-Vis spectrum with a maximum from 380 to 420 nm; and (b) an anionic dispersing agent for protecting the human skin from browning and skin aging.

3 Claims, 4 Drawing Sheets

USE OF TRANSMISSION DYES FOR PROTECTING HUMAN SKIN FROM BROWNING AND AGEING

The present invention relates to the use of specific transmission dyes for protecting human hair and skin against UV radiation and skin aging and preventing tanning and cosmetic or dermatological compositions comprising these dyes.

It is known that certain photostable organic UV filters, for example bis-ethylhexyloxyphenol methoxyphenyl triazine, methylene bis-benzotriazolyl tetramethylbutylphenol disodium phenyl dibenzimidazole tetrasulfonate or terephthalylidene dicamphor sulfonic acid or butyl methoxy dibenzoyl methane which is photo-stabilized with octocrylene exhibit pronounced UV filtering properties in the UV-A range up to 380 nm. In the range from 380 nm to 420 nm no satisfactory UV protection can be achieved.

However, it is known that in the region >380 nm the sun light significantly contributes to skin aging and enhanced skin cancer risk.

Surprisingly it was found that specific UV absorbers which have absorption maxima above 380 nm show no significant color when applied to the skin.

Therefore the present invention relates to the use of an aqueous dispersion comprising
(a) a micronized sparingly soluble organic compound which has a UV-Vis spectrum with a maximum from 380 to 420 nm; and
(b) an anionic dispersing agent for protecting the human skin from browning and skin aging.

A BRIEF DESCRIPTION OF THE DRAWING

X-ray diffractograms of the compound of formula (101)

Figure 1:
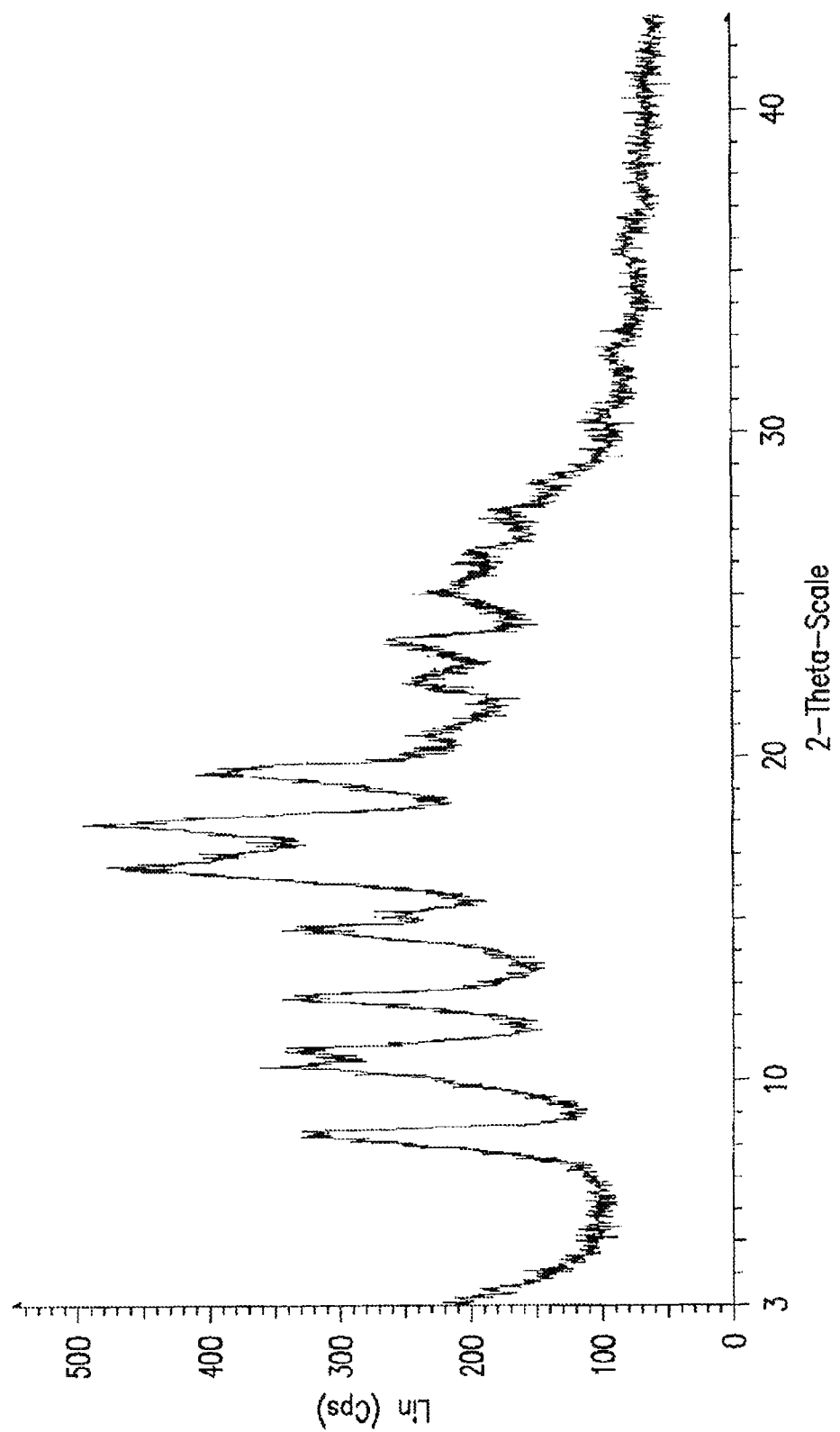
FIG. 1 is Form A: (partly) amorphous product, precipitated from solution with Deionat.
Figure 2:
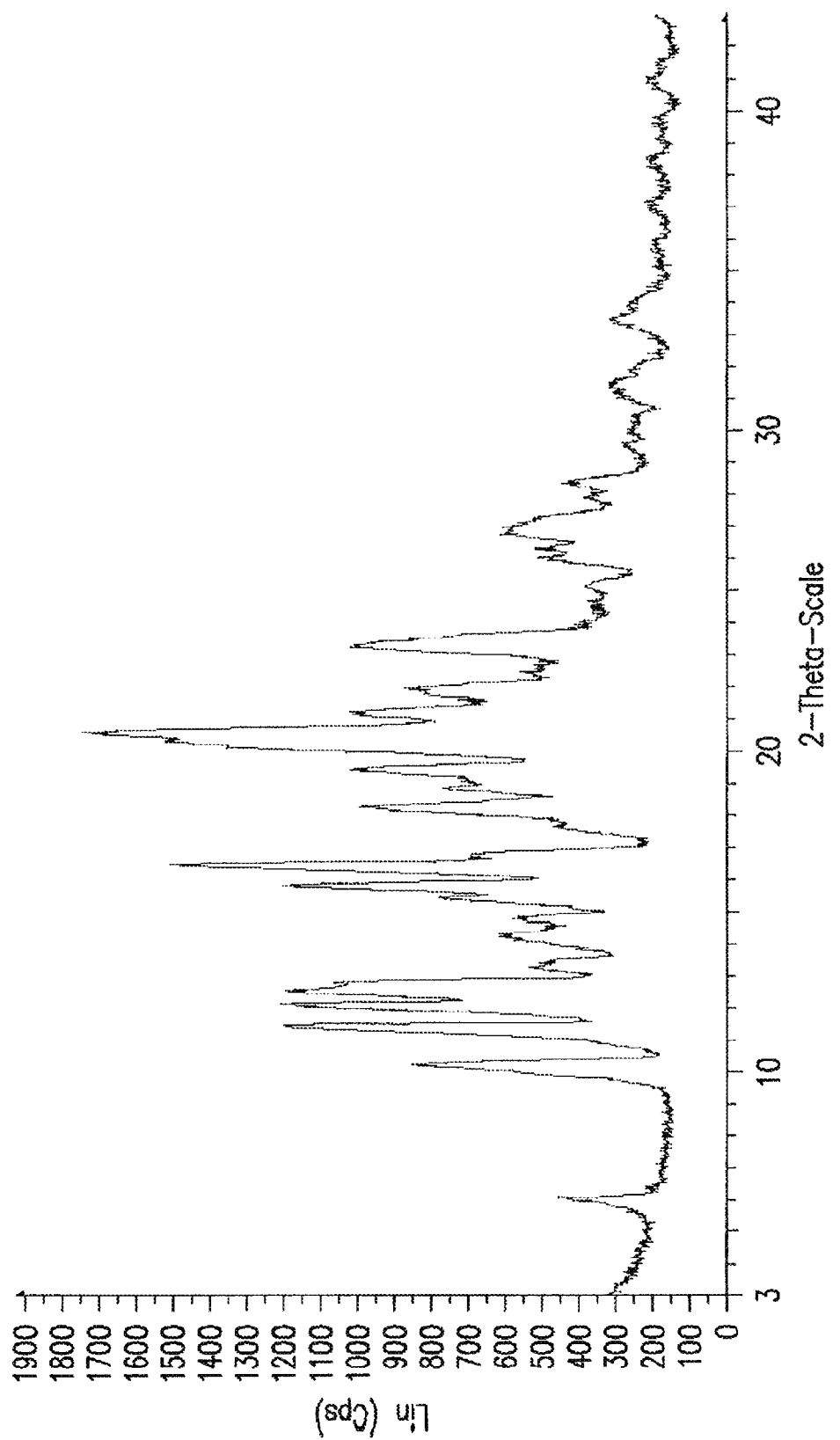
FIG. 2 is Form B: raw product from the reaction mixture/reaction mass before cristallisation.
Figure 3:
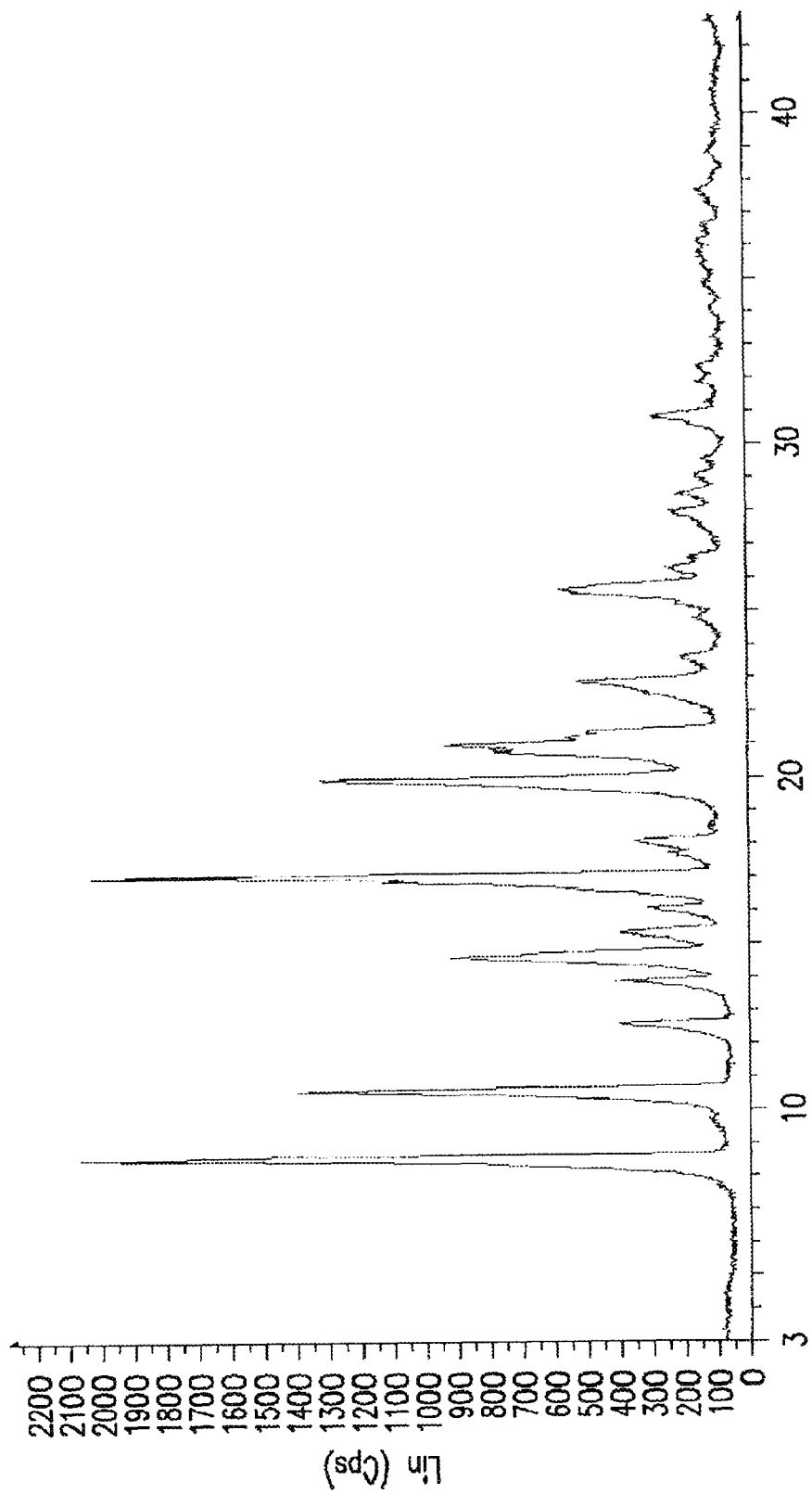
FIG. 3 is Form C: crystals obtained from recrystalization from 2-methoxyethanol.
Figure 4:
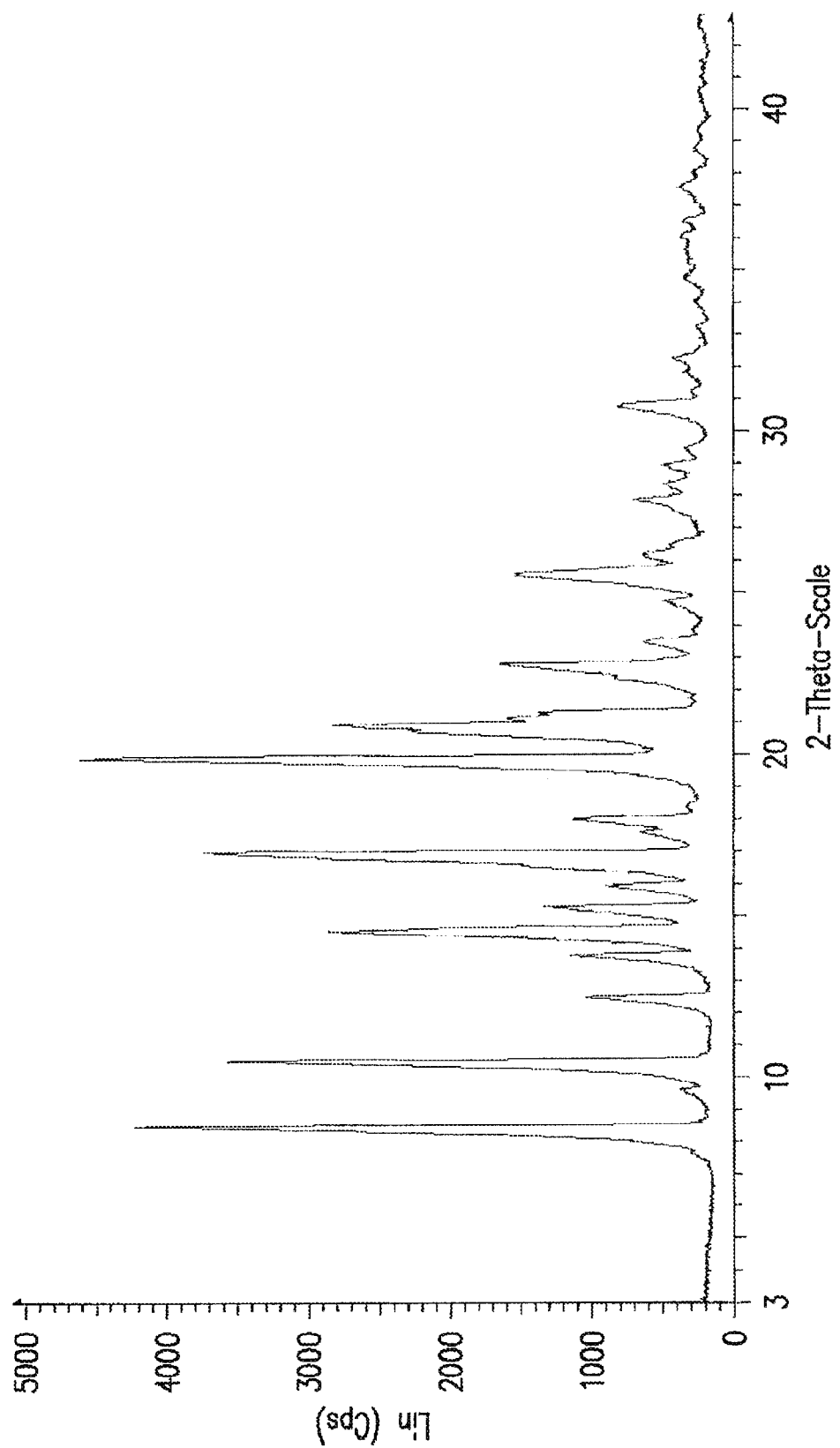
FIG. 4 is Form D: Crystals from recrystallization from N-methyl-pyrrolidone/1-propanol.

Preferably the organic micronized UV absorbers are selected from benzophenone derivatives.

More preferably they correspond to the compounds of formula

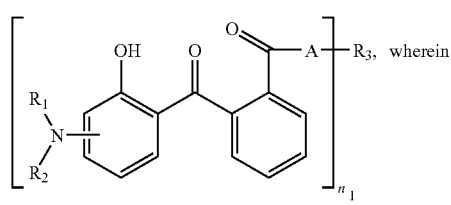

(1)

$R_1$ and $R_2$ independently from each other are $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;
$n_1$ is a number from 1 to 4;
when $n_1$=1,
$R_3$ is a saturated or unsaturated heterocyclic radical; hydroxy-$C_1$-$C_5$alkyl; cyclohexyl which is optionally substituted with one or more $C_1$-$C_5$alkyl; phenyl, which is optionally substituted with a heterocyclic radical, aminocarbonyl or $C_1$-$C_5$alkylcarboxy;
when $n_1$ is 2,
$R_3$ is an alkylene-, cycloalkylene, alkenylene or phenylene radical which is optionally substituted by a carbonyl- or carboxy group; a radical of formula

or
$R_3$ together with A forms a bivalent radical of the formula

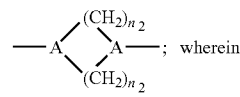
(1a)

$n_2$ is a number from 1 to 3;
when $n_1$ is 3,
$R_3$ is an alkanetriyl radical;
wenn $n_1$ is 4,
$R_3$ is an alkanetetrayl radical;
A is —O—; or —N($R_5$)—; and
$R_5$ is hydrogen; $C_1$-$C_5$alkyl; or hydroxy-$C_1$-$C_5$alkyl.

$C_1$-$C_{20}$alkyl denotes a linear or branched, unsubstituted or substituted alkyl group such as, for example, methyl, ethyl, propyl, isopropyl, n-butyl, n-hexyl, cyclohexyl, n-decyl, n-dodecyl, n-octadecyl, eicosyl, methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octyl-phenoxyethyl, 3-(2,4-di-tert-amylphenoxy)-propyl, ethoxycarbonylmethyl-2-(2-hydroxy-ethoxy)ethyl or 2-furylethyl.

$C_2$-$C_{20}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_3$-$C_{10}$cycloalkyl is for example cyclopropyl, cyclobutyl, cyclopentyl, cycloheptyl, cyclooctyl, cyclononyl or cyclodecyl and preferably cyclohexyl. These radicals may be substituted, for example by one or more oder equal or different $C_1$-$C_4$alkyl radicals, preferably by methyl, and/or hydroxy. If cycloalkyl radicals are substituted by one or more radicals, they are preferably substituted by one, two or four, preferably by one or two equal or radicals.

$C_3$-$C_{10}$cycloalkenyl is for example cyclopropenyl, cyclobutenyl, cyclopentenyl, cycloheptenyl, cyclooctenyl, cyclononenyl or cyclodecenyl and preferably cyclohexenyl. These radicals may be substituted with one or more equal or different $C_1$-$C_4$alkyl radical, preferably with methyl, and/or hydroxy. If cycloalkenyl radicals are substituted with one or more radicals they are preferably substituted with one, two, three or four, preferably with one or two equal or different radicals.

Hydroxy-substituted $C_1$-$C_5$alkyl groups are for example hydroxymehtyl, hydroxyethyl, hydroxypropyl, hydroxybutyl or hydroxypentyl.

An alklyene radical is preferably a $C_1$-$C_{12}$alkylene radical, like for example methylene, ethylene, propylene, butylene, hexylene or octylene.

The alklyene radicals may optionally be substituted by one or more $C_1$-$C_5$alkyl radicals.

If $R_1$ and $R_2$ are heterocyclic radicals, these comprise one, two, three or four equal or different ring hetero atoms. Special preference is given to heterocycles which contain one, two or three, especially one or two, identical or different hetero atoms. The heterocycles may be mono- or poly-cyclic, for example mono-, bi- or tri-cyclic. They are preferably mono- or bi-cyclic, especially monocyclic. The rings preferably contain 5, 6 or 7 ring members. Examples of monocyclic and bicyclic heterocyclic systems from which radicals occurring in the compounds of formula (1) or (2) may be derived are, for example, pyrrole, furan, thiophene, imidazole, pyrazole, 1,2,3-triazole, 1,2,4-triazole, pyridine, pyridazine, pyrimidine, pyrazine, pyran, thiopyran, 1,4-dioxane, 1,2-oxazine, 1,3-oxazine, 1,4-oxazine, indole, benzothio-phene, benzofuran, pyrrolidine, piperidine, piperazine, morpholine and thiomorpholine.

Most preferably the benzophenone derivative used for the present invention corresponds to formula

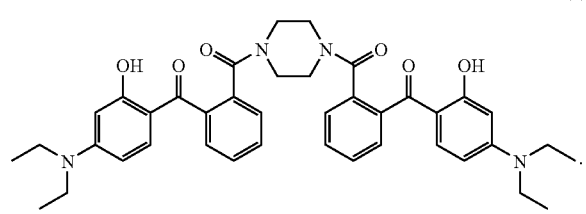

(2)

Furthermore, the following benzophenone derivatives are of interest:

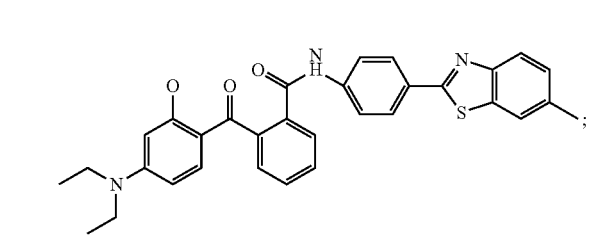

(3)

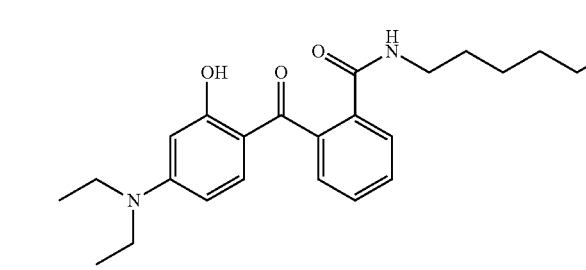

(6)

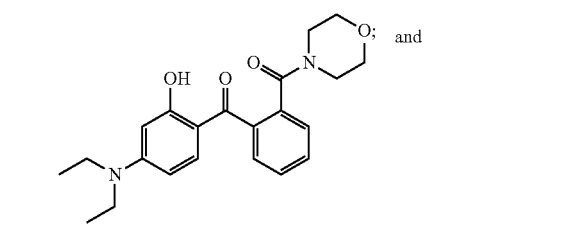

The compounds of formula (1) may be prepared according to known methods as described for example in EP-1,046,391 or WO 04/052837.

Sparingly soluble organic compounds which are used in the present invention are present in the micronized state. They may be prepared by any known process suitable for the preparation of microparticles, for example: wet-milling, wet-kneading, spray-drying from a suitable solvent, by expansion according to the RESS process (Rapid Expansion of Supercritical Solutions) of supercritical fluids (e.g. $CO_2$, by reprecipitation from suitable solvents, including supercritical fluids (GASR process=Gas Anti-Solvent Recrystallisation/PCA process=Precipitation with Compressed Anti-solvents).

As milling apparatus for the preparation of the sparingly soluble micronised organic compounds there may be used, for example, a jet mill, ball mill, vibratory mill or hammer mill, preferably a high-speed mixing mill. Even more preferable mills are modern ball mills; manufacturers of these types of mill are, for example, Netzsch (LMZ mill), Drais (DCP-Viscoflow or Cosmo), Buhler AG (centrifugal mills) or Bachhofer.

Examples of kneading apparatus for the preparation of the micronised organic UV absorbers are typical sigma-blade batch kneaders but also serial batch kneaders (IKA-Werke) or continuous kneaders (Continua from Werner und Pfleiderer).

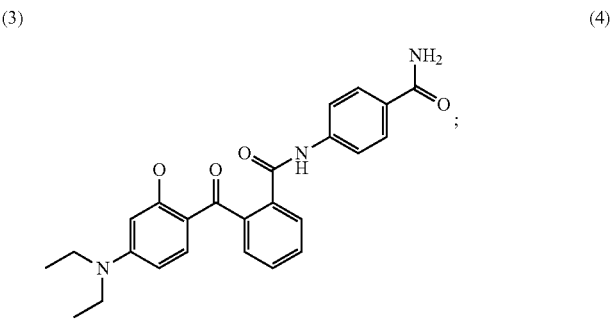

(4)

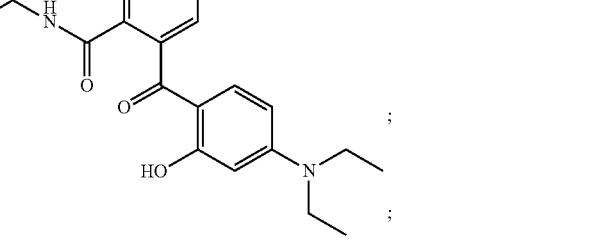

(5)

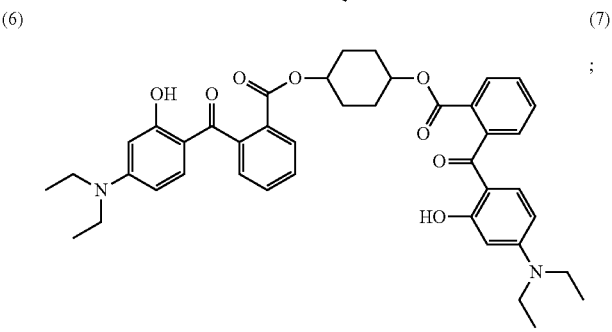

(7)

The grinding of the sparingly soluble organic compounds used in the present invention is preferably carried out with a grinding aid.

The dispersing agent (b) is used as a low molecular weight grinding aid for all the above micronisation processes.

Useful anionic, non-ionic or amphoteric surfactants are disclosed below in the sections entitled "specific dispersing agents".

Preferred useful grinding aids for an aqueous dispersion are anionic surfactants with a HLB (Hydrophile-Lipophile Balance) value higher than 8, more preferably higher than 10.

Any conventionally usable anionic, non-ionic or amphoteric surfactants can be used as dispersing agents (component (b)). Such surfactant systems may comprise for example: carboxylic acids and their salts: alkaline soap of sodium, potassium and ammonium, metallic soap of calcium or magnesium, organic basis soap such as Lauric, myristic, palmitic, stearic and oleic acid etc . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Fatty alcohol polyglycolether such as laureth-n, myreth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 100 mol of ethylene oxide with polyols. Fatty acid and polyglycerol ester such as monostearate glycerol, diisostearoyl polyglyceryl-3-d iisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/ methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates [Texapon N70] or sodium myreth sulfates [Texapon K14S], sulfosuccinates, aceyl isothionates, alkanolamide sulfates, taurines, methyl taurines, imidazole sulfates. Zwitterionic or amphoteric surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines.

Examples of suitable mild surfactants as dispersing agents, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins. Non ionic surfactants such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate.[Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate .[Hetester PCS], propylene glycol isoceth-3 acetate [Hetester PHA], cetearyl alcohol and ceteth-12 and oleth-12 [Lanbritol Wax N 21], PEG -6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina K D], propylene glycol stearate [Tegin P], cetearyl Alcohol and Sodium cetearyl sulfate [Lanette N, Cutina L E, Crodacol G P], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

Most preferred dispersing agents (b) are sodium alkyl sulfates or sodium alkyl ether sulfates, such as sodium laureth sulfate [Texapon N70 from Cognis] or sodium myreth sulfate [Texapon K14 S from Cognis].

The specific dispersing agents may be used in an amount of, for example, from 1 to 30% by weight, especially from 2 to 20% by weight and preferably from 3 to 10% by weight, based on the total weight of the composition.

Useful solvents are water, brine, (poly-)ethylene glycol, glycerol or cosmetically acceptable oils. Other useful solvents are disclosed below in the sections entitled "Esters of fatty acids", "Natural and synthetic triglycerides, including glyceryl esters and derivatives", "Pearlescent waxes", "Hydrocarbon oils" and "Silicones or siloxanes".

The micronised sparingly soluble organic compounds so obtained usually have an average particle size from 0.02 to 2 micrometres, preferably from 0.03 to 1.5 micrometres and more especially from 0.05 to 1.0 micrometres.

The aqueous dispersion used in the present invention generally comprises 30-60, preferably 35 to 55 parts of the sparingly soluble organic micronized substance;

2-20, preferably 2 to 20 parts of the dispersing agent;

0.1-1 part, preferably 0.1 to 0.5 parts of a thickening agent (for example xanthan gum); and 20-68 parts of water;

The cosmetic formulations or pharmaceutical compositions according to the present invention can also comprise one or more than one further UV filter as listed in Table 1:

TABLE 1

Suitable UV filter substances and adjuvants which can be additionally used with the UV absorbers according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts (Mexoryl SL) | 56039-58-8 |
| 11 | 1-[4-(1,1-dimethylethyl)phenyl]-3-(4-methoxyphenyl)propane-1,3-dione (Avobenzone) | 70356-09-1 |
| 12 | Methyl N,N,N-trimethyl-4-[(4,7,7-trimethyl-3-oxobicyclo[2,2,1]hept-2-ylidene)methyl]anilinium sulphate (Mexoryl SO) | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; octocrylene | 6197-30-4 |
| 30 | 2-ethylhexyl 4-(dimethylamino)benzoate | 21245-02-3 |
| 31 | 2-ethylhexyl 4-methoxycinnamate; octyl methoxy cinnamate | 5466-77-3 |
| 32 | 2-ethylhexyl salicylate | 118-60-5 |
| 33 | Benzoic acid,4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine (Octyl Triazone) | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid] (Cibafast H) | 90457-82-2 |
| 42 | Titanium dioxide (primary particle size 10-50 nm) For example T805 or Eusolex T-AVO, Eusolex T-2000, Titaniumdioxid VT 817 | 13463-67-7 |
| 44 | Zinc oxide (primary particle size 20-100 nm) For example Zinc oxide NDM, Zinc oxide Z-Cote HP1, Nanox Zinc oxide | 1314-13-2 |
| 45 | 2,2'-Methylene-bis-[6-(2H-benzotriazol-2-yl)-4-(1,1,3,3-tetramethyl-butyl)-phenol](Tinosorb M) | 103597-45-1 |
| 46 | 2,4-bis{[4-(2-ethylhexyloxy)-2-hydroxy]-phenyl}-6-(4-methoxyphenyl)-(1,3,5)-triazine (Tinosorb S) | 187393-00-6 |
| 47 | 1H-Benzimidazole-4,6-disulfonic acid, 2,2'-(1,4-phenylene)bis-, di-sodium salt | 180898-37-7 |
| 48 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester; diethylhexyl butamido triazone (Uvasorb HEB) | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane (Mexoryl XL) | 155633-54-8 |
| 50 | Dimethicodiethylbenzalmalonate; Polysilicone 15 (Parsol SLX) | 207574-74-1 |
| 51 | Benzenesulfonic acid, 3-(2H-benzotriazol-2-yl)-4-hydroxy-5-(1-methylpropyl)-, monosodium salt (Tinogard HS) | 92484-48-5 |
| 52 | Benzoic acid, 2-[4-(diethylamino)-2-hydroxybenzoyl]-, hexyl ester (Uvinul A Plus) | 302776-68-7 |
| 53 | 1-Dodecanaminium, N-[3-[[4-(dimethylamino)benzoyl]amino]propyl]-N,N-dimethyl-, salt with 4-methylbenzenesulfonic acid (1:1) (Escalol HP6 10) | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate) (Glyceryl PABA) | 136-44-7 |
| 62 | Benzeneacetic acid, 3,4-dimethoxy-α-oxo- | 4732-70-1 |

TABLE 1-continued

Suitable UV filter substances and adjuvants which can be additionally used with the UV absorbers according to the present invention

| No. | Chemical Name | CAS No. |
|---|---|---|
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate (Neo Heliopan AP) | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- (Uvasorb K2A) | 288254-16-0 |
| 67 | Merocyanine derivatives as described in WO 2004006878, WO2006032741, IPCOM000022279D and in IP.COM JOURNAL (2005), 5(7B), 18 | |

68

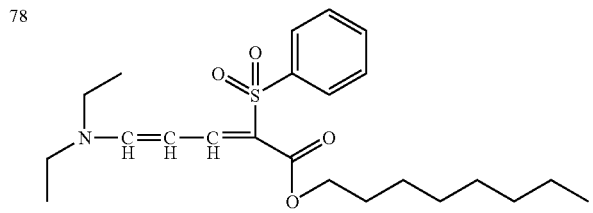

| 69 | sterols (cholesterol, lanosterol, phytosterols), as described in WO0341675 | |
| 70 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 71 | alpha-lipoic-acid as described in DE 10229995 | |
| 72 | synthetic organic polymers as described in EP 1371358, [0033]-[0041] | |
| 73 | phyllosilicates as described in EP 1371357 [0034]-[0037] | |
| 74 | silica compounds as described in EP1371356, [0033]-[0041] | |
| 75 | inorganic particles as described in DE10138496 [0043]-[0055] | |
| 76 | latex particles as described in DE10138496 [0027]-[0040] | |
| 77 | 1H-Benzimidazole-4,6-disulfonic acid, 2,2'-(1,4-phenylene)bis-, disodium salt; Bisimidazylate (Neo Heliopan APC) | 180898-37-7 |

78

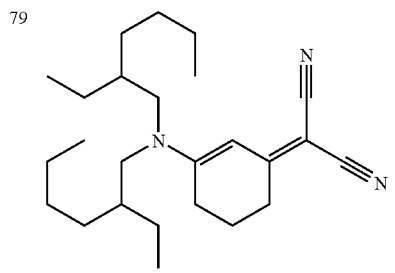

79

TABLE 1-continued

Suitable UV filter substances and adjuvants which can be
additionally used with the UV absorbers according to the present invention

| No. | Chemical Name | CAS No. |
|---|---|---|
| 80 | 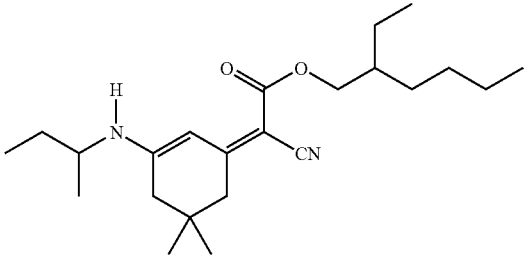<br>E or Z isomer or mixture of E/Z isomers | |
| 81 | 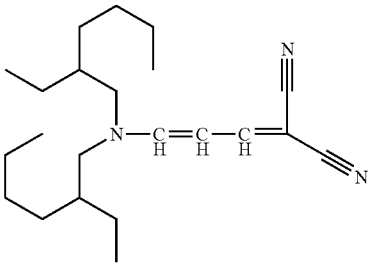 | |
| 82 | Di-2-ethylhexyl-3,5-dimethoxy-4-hydroxy-benzalmalonate (Oxynex ST, EMD Chemicals, as described in US 20040247536) | |
| 83 | 2,4,6-Tris-1,1',4',1''-terphenyl-4-yl-1,3,5-triazine | |
| 84 | 2,4,6-Tris(p-biphenylyl)-s-triazine | 31274-51-8 |

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, of one UV absorber or UV absorber mixtures.

Preference is given to the use of mixing ratios of the compound of formula (1) according to the present invention and optionally further light-protective agents from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase UV absorption.

The compounds of formula (1) may also be used as an anti-wrinkle perception modifier.

This is a further object of the present invention.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds as like fatty alcohols, esters of fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers, djuvants and additives, super-fatting agents, surfactants, consistency regulators/thickeners and rheology modifiers, polymers, biogenic active ingredients, deodorising active ingredients, anti-dandruff agents, antioxidants, hydrotropic agents, preservatives, bacteria-inhibiting agents, perfume oils, colourants, polymeric beads or hollow spheres as SPF enhancers.

Cosmetic or Pharmaceutical Preparations

Cosmetic or pharmaceutical formulations are contained in a wide variety of cosmetic preparations. There come into consideration, for example, especially the following preparations: skin-care preparations, bath preparations, cosmetic personal care preparations, foot-care preparations, light-protective preparations, skin-tanning preparations, depigmenting preparations, insect-repellents, deodorants, antiperspirants, preparations for cleansing and caring for blemished skin, hair-removal preparations in chemical form (depilation), shaving preparations, fragrance preparations, cosmetic hair-treatment preparations, Presentation Forms The final formulations listed may exist in a wide variety of presentation forms, for example:
- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a powder, a lacquer, a tablet or make-up,
- in the form of a stick,
- in the form of a spray (spray with propellent gas or pump-action spray) or an aerosol,
- in the form of a foam, or
- in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The cosmetic preparation according to the invention is distinguished by excellent protection of human skin against the damaging effect of sunlight.

EXAMPLES

Preparation of UV Absorbers

Example 1

Preparation of the Compound of Formula

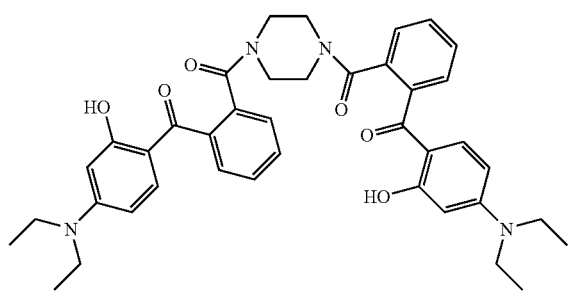

(101)

59.0 g 3 diethylamino-dibenzo-oxepin of formula

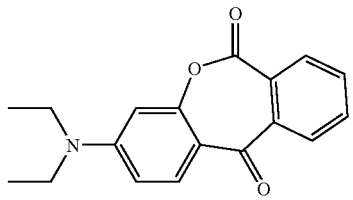

(101a)

(prepared according to Example 1 of WO 204/052837) are dissolved in 250 ml acetic acid ethyl ester at room temperature.

8.6 g piperazine are added to this solution with stirring whereas the temperature rises to 40° C.

The product precipitates during adding of the reaction mass.

Then the suspension is stirred for about 3 h under reflux, filtered off and the residue is recrystallized from 2-methoxyethanol.

After drying of the citric yellow crystals 67 g of the end product are obtained.

Fp=253-256° C.

The compound of formula (101) can be obtained in different forms. The single crystal forms are characterized by their x-ray diffractograms.

X-ray Diffractograms of the Compound of Formula (101)

Form A: (partly) amorphous product, precipitated from solution with Deionat:

| 2-Theta Scale | Lin [Cps] | 2-Theta Scale | Lin [Cps] | 2-Theta Scale | Lin [Cps] |
|---|---|---|---|---|---|
| 8.2 | 330 | 14.5 | 340 | 22.0 | 250 |
| 10.2 | 360 | 16.5 | 480 | 23.5 | 270 |
| 10.6 | 330 | 17.7 | 500 | 25.0 | 240 |
| 12.3 | 340 | 18.2 | 400 | 27.0 | 190 |

Form B: raw product from the reaction mixture/reaction mass before cristallisation:

| 2-Theta Scale | Lin [Cps] | 2-Theta Scale | Lin [Cps] | 2-Theta Scale | Lin [Cps] |
|---|---|---|---|---|---|
| 6 | 470 | 15.8 | 1220 | 21.0 | 1000 |
| 10.2 | 870 | 16.2 | 1520 | 21.7 | 870 |
| 11.3 | 1200 | 18.0 | 980 | 23.0 | 1000 |
| 12.0 | 1220 | 19.3 | 1040 | 26.7 | 570 |
| 12.3 | 1200 | 20.0 | 1750 | | |

Form C: cristals obtained from recrystalization from 2-methoxyethanol:

| 2-Theta Scale | Lin [Cps] | 2-Theta Scale | Lin [Cps] | 2-Theta Scale | Lin [Cps] |
|---|---|---|---|---|---|
| 8.5 | 2080 | 15.3 | 420 | 20.8 | 950 |
| 10.5 | 1450 | 11.8 | 2050 | 22.8 | 530 |
| 12.7 | 400 | 18.0 | 350 | 25.7 | 600 |
| 13.8 | 430 | 19.8 | 1350 | 30.7 | 300 |
| 14.5 | 940 | | | | |

Form D: Crystals from recrystallization from N-methyl-pyrrolidone/1-propanol:

| 2-Theta Scale | Lin [Cps] | 2-Theta Scale | Lin [Cps] | 2-Theta Scale | Lin [Cps] |
|---|---|---|---|---|---|
| 7.3 | 4300 | 15.2 | 1400 | 21.0 | 2800 |
| 10.0 | 3530 | 16.2 | 930 | 22.7 | 1650 |
| 12.5 | 1000 | 17.0 | 3800 | 28.0 | 700 |
| 13.8 | 1220 | 18.0 | 1150 | 30.8 | 800 |
| 14.5 | 2800 | 19.5 | 4600 | | |

Examples 2-5

Dispersion Formulations

General Dispersion Formulation

| | |
|---|---|
| Sparingly soluble organic micronized substance | 30-60 parts |
| dispersing agent (for example APG, C12-C14 ethersulfates) | 2-20 parts |
| water | 20-68 parts |
| thickening agent (for example xanthan gum) | 0.1-1 part |

Dispersions

EXAMPLE 2

| Sparingly soluble micronized substance | Dispersing agent | water | Thickening agent |
|---|---|---|---|
| Compound of formula (101) 40% | Decylpoly-glucoside 7.5% | 52% | xanthan gum (0.2% + 0.3% propylene glycol) |

Results for Example 2:
E1.1: 600 bei 392 nm;
37% of the absoprtion at >398 nm (visible range);
57% of the absoprtion at >380 nm.
Absorption minimum from 290 to 340 nm

EXAMPLE 3

| Sparingly soluble micronized substance | Dispersing agent | water | Thickening agent |
|---|---|---|---|
| Compound of formula (101) 50% | Laurylether sulfate 3.5% | 46% | xanthan gum (0.2% + 0.3% propylene glycol) |

Results for Example 3:
E1.1: 700 at 391 nm:
ca. 20% of the absoprtion at >398 nm (visible range);
absorption minimum from 290 to 340 nm.

EXAMPLE 4

| Sparingly soluble micronized substance | Dispersing agent | water | Thickening agent |
|---|---|---|---|
| Compound of formula (101) 50% | Myrystylehter (EO3) sulfate 5% | 44.5% | xanthan gum (0.2% + 0.3% propylene glycol) |

Results for Example 4:
E1.1: 680 at 390 nm;
ca. 22% of the absoprtion at >398 nm (visible range);
absorption minimum from 290 to 340 nm

EXAMPLE 5

| Sparingly soluble micronized substance | Dispersing agent | water | Thickening agent |
|---|---|---|---|
| Compound of formula (101) 50% | Decylpolyglucoside 5% PotassiumCetyl-phosphate (Amphisol K from DSM) 1.5% | 43.2% | xanthan gum (0.1% + 0.2% propylene glycol) |

Results for Example 4:
E1.1: 650 at 391 nm;
ca. 22% of the absoprtion at >398 nm (visible range);
absorption minimum from 290 to 340 nm With this method a micropigment dispersion of a UV absorber is obtained.

Application Examples

EXAMPLE 6

UV-A/UV-B Daily Care UV Protection Lotion

| INCI-Name | % w/w (as supplied) | | | | | |
|---|---|---|---|---|---|---|
| | 6a | 6b | 6c | 6d | 6e | 6f |
| Oleth-3 Phosphate | 0.60 | 0.60 | 0.60 | 0.60 | 0.60 | 0.60 |
| Glyceryl stearate Citrate | 0.50 | | 1.00 | | 1.50 | 0.80 |
| Steareth-21 | 2.50 | 2.50 | 1.50 | 2.50 | 0.50 | 1.50 |
| Steareth-2 | 1.00 | 1.00 | 1.00 | 1.00 | 1.00 | 1.00 |
| Cetyl Alcohol | 0.80 | 0.80 | 0.80 | 0.80 | 0.80 | 0.80 |
| Stearyl Alcohol | 1.50 | 1.50 | 1.50 | 1.50 | 1.50 | 1.50 |
| Tribehenin | 0.80 | 0.80 | 0.80 | 0.80 | 0.80 | 0.80 |
| Isohexadecane | 8.00 | 8.00 | 8.00 | 8.00 | 8.00 | 8.00 |
| Compound of the formula (a4) | 2.00 | 1.00 | | | | |
| Compound of the formula (c4) | | | 1.30 | 1.00 | | |
| Compound of the formula (d4) | | | 1.00 | 1.50 | | |
| Compound of the formula (e4) | | | 1.00 | 1.00 | 2.00 | |
| Compound of the formula (g4) | | | 1.00 | | 1.50 | |
| Compound of the formula (h2) | | | 1.00 | | | 2.00 |
| Water | qs to 100 | qs to 100 | qs to 100 | qs to 100 | qs to 100 | qs to 100 |
| Glycerin | 2.00 | 2.00 | 2.00 | 2.00 | 2.00 | 2.00 |
| UV-absorber dispersion as described in example 3; compound of formula (101) | 1.00 | | 5.00 | | 4.00 | |

EXAMPLE 6-continued

UV-A/UV-B Daily Care UV Protection Lotion

| INCI-Name | % w/w (as supplied) | | | | | |
|---|---|---|---|---|---|---|
| | 6a | 6b | 6c | 6d | 6e | 6f |
| UV-absorber dispersion as described in example 5; compound of formula (101) | 1.00 | 3.00 | | 11.00 | 2.00 | 6.00 |
| Micropigment dispersion of 2,4,6-Tris(p-biphenylyl)-s-triazine [CAS No. 31274-51-8] | 4.00 | 4.00 | 4.00 | 4.00 | 4.00 | 4.00 |
| Disodium EDTA | 0.10 | 0.10 | 0.10 | 0.10 | 0.10 | 0.10 |
| Octocrylene | 6.00 | | 4.00 | 4.00 | 10.00 | 4.00 |
| Ethylhexyl methoxy cinnamate | 2.00 | 4.00 | 4.00 | | 2.00 | 6.00 |
| Water | 20.00 | 20.00 | 20.00 | 20.00 | 20.00 | 20.00 |
| Diazolidinyl Urea (and) Iodopropynyl Butylcarbamate | 0.15 | 0.15 | 0.15 | 0.15 | 0.15 | 0.15 |
| Propylene Glycol | 4.00 | 4.00 | 4.00 | 4.00 | 4.00 | 4.00 |
| Sodium Acrylates Copolymer (and) Paraffinium Liquidum (and) PPG-1 Trideceth-6 | 1.50 | 1.50 | 1.50 | 1.50 | 1.50 | 1.50 |
| Cyclopentasiloxane | 4.00 | 4.00 | 4.00 | 4.00 | 4.00 | 4.00 |
| PEG-12 Dimethicone | 2.00 | 2.00 | 2.00 | 2.00 | 2.00 | 2.00 |
| Tocopheryl Acetate | 0.45 | 0.45 | 0.45 | 0.45 | 0.45 | 0.45 |
| Water (and) Citric Acid | Qs | Qs | Qs | Qs | Qs | Qs |
| Fragrance | Qs | Qs | Qs | Qs | Qs | Qs |

EXAMPLE 7

UV-A/UV-B Daily Care UV Protection Lotion

| INCI-Name | % w/w (as supplied) | | | | | |
|---|---|---|---|---|---|---|
| | 7a | 7b | 7c | 7d | 7e | 7f |
| Oleth-3 Phosphate | 0.60 | 0.60 | 0.60 | 0.60 | 0.60 | 0.60 |
| Steareth-21 | 2.50 | 2.50 | 2.50 | 2.50 | 2.50 | 2.50 |
| Steareth-2 | 1.00 | 1.00 | 1.00 | 1.00 | 1.00 | 1.00 |
| Cetyl Alcohol | 0.80 | 0.80 | 0.80 | 0.80 | 0.80 | 0.80 |
| Stearyl Alcohol | 1.50 | 1.50 | 1.50 | 1.50 | 1.50 | 1.50 |
| Tribehenin | 0.80 | 0.80 | 0.80 | 0.80 | 0.80 | 0.80 |
| Isohexadecane | 8.00 | 8.00 | 8.00 | 8.00 | 8.00 | 8.00 |
| Ethylhexyl Methoxycinnamate | 5.00 | 2.00 | 8.00 | 10.00 | 3.00 | |
| Compound of the formula (i2) | 2.00 | 1.00 | | | | |
| Compound of the formula (k2) | | 1.30 | 2.00 | 4.00 | 1.30 | |
| Compound of the formula (h2) | | 1.00 | 1.50 | | | 1.30 |
| Compound of the formula (p2) | | 1.00 | | 2.00 | | 3.00 |
| Compound of the formula (r2) | | 1.00 | | | 1.50 | |
| Compound of the formula (t2) | | 1.00 | | 1.30 | | 2.00 |
| Water | qs to 100 | qs to 100 | qs to 100 | qs to 100 | qs to 100 | qs to 100 |
| Glycerin | 2.00 | 2.00 | 2.00 | 2.00 | 2.00 | 2.00 |
| UV-absorber dispersion as described in example 3; compound of formula (101) | | | 3.00 | | 3.00 | |
| UV-absorber dispersion as described in example 5; compound of formula (101) | 1.00 | 3.00 | | 11.00 | 2.00 | 6.00 |
| Micropigment dispersion of 2,4,6-Tris(p-biphenylyl)-s-triazine [CAS No. 31274-51-8] | 4.00 | 4.00 | 4.00 | 4.00 | 4.00 | 4.00 |
| Octocrylene | 2.00 | 8.00 | 5.00 | | 1.00 | 6.00 |
| Avobenzone | | 2.50 | 5.00 | | 3.00 | |
| Disodium EDTA | 0.10 | 0.10 | 0.10 | 0.10 | 0.10 | 0.10 |
| Water | 20.00 | 20.00 | 20.00 | 20.00 | 20.00 | 20.00 |
| Diazolidinyl Urea (and) Iodopropynyl Butylcarbamate | 0.15 | 0.15 | 0.15 | 0.15 | 0.15 | 0.15 |
| Propylene Glycol | 4.00 | 4.00 | 4.00 | 4.00 | 4.00 | 4.00 |
| Sodium Acrylates Copolymer (and) Paraffinium Liquidum (and) PPG-1 Trideceth-6 | 1.50 | 1.50 | 1.50 | 1.50 | 1.50 | 1.50 |
| Cyclopentasiloxane | 4.00 | 4.00 | 4.00 | 4.00 | 4.00 | 4.00 |
| PEG-12 Dimethicone | 2.00 | 2.00 | 2.00 | 2.00 | 2.00 | 2.00 |
| Tocopheryl Acetate | 0.45 | 0.45 | 0.45 | 0.45 | 0.45 | 0.45 |
| Water (and) Citric Acid | Qs | Qs | Qs | Qs | Qs | Qs |
| Fragrance | Qs | Qs | Qs | Qs | Qs | Qs |

EXAMPLE 8

UV-A/UV-B Daily Care UV Protection Lotion

| INCI-Name | % w/w (as supplied) | | | | | |
|---|---|---|---|---|---|---|
| | 8a | 8b | 8c | 8d | 8e | 8f |
| Oleth-3 Phosphate | | 0.60 | 0.60 | 0.60 | 0.60 | 0.60 |
| Potassium Cetyl Phosphate | 2.00 | | 1.50 | | 1.00 | |
| Steareth-21 | | 2.50 | | 2.50 | 1.00 | 2.50 |
| Steareth-2 | | 1.00 | 1.00 | 1.00 | 1.00 | 1.00 |
| Cetyl Alcohol | 0.80 | 0.80 | 0.80 | 0.80 | 0.80 | 0.80 |
| Stearyl Alcohol | 1.50 | 1.50 | 1.50 | 1.50 | 1.50 | 1.50 |
| Tribehenin | 0.80 | 0.80 | 0.80 | 0.80 | 0.80 | 0.80 |
| Isohexadecane | 8.00 | 8.00 | 8.00 | 8.00 | 8.00 | 8.00 |
| Ethylhexyl Methoxycinnamate | 3.00 | 3.00 | 3.00 | 3.00 | 3.00 | 3.00 |
| Compound of the formula (u2) | 2.00 | | 1.10 | 1.10 | | |
| Compound of the formula (v2) | | 1.30 | 1.10 | | | 1.10 |
| Compound of the formula (x2) | | | 1.50 | | 1.10 | |
| Compound of the formula (s2) | | | 1.10 | 2.00 | | |
| Compound of the formula (q2) | 1.10 | | 1.10 | | 1.50 | |
| Compound of the formula (b4) | | 1.10 | 1.10 | 8.00 | 2.00 | 2.00 |
| Water | qs to 100 | qs to 100 | qs to 100 | qs to 100 | qs to 100 | qs to 100 |
| UV-absorber dispersion as described in example 5; compound of formula (101) | | 3.00 | | 11.00 | 2.00 | 6.00 |
| Glycerin | 2.00 | 2.00 | 2.00 | 2.00 | 2.00 | 2.00 |
| UV-absorber dispersion as described in example 5; compound of formula (101) | | 3.00 | | 11.00 | 2.00 | 6.00 |
| UV-absorber dispersion as described in example 3; compound of formula (101) | 3.00 | | 3.00 | | 3.00 | |
| Micropigment dispersion of 2,4,6-Tris(p-biphenylyl)-s-triazine [CAS No. 31274-51-8] | 4.00 | | 4.00 | | 4.00 | |
| Octocrylene | 4.00 | 4.00 | 4.00 | 4.00 | 4.00 | 4.00 |
| Avobenzone | 1.00 | | | 2.00 | 4.00 | |
| Disodium EDTA | 0.10 | 0.10 | 0.10 | 0.10 | 0.10 | 0.10 |
| Water | 20.00 | 20.00 | 20.00 | 20.00 | 20.00 | 20.00 |
| Diazolidinyl Urea (and) Iodopropynyl Butylcarbamate | 0.15 | 0.15 | 0.15 | 0.15 | 0.15 | 0.15 |
| Propylene Glycol | 4.00 | 4.00 | 4.00 | 4.00 | 4.00 | 4.00 |
| Sodium Acrylates Copolymer (and) Paraffinium Liquidum (and) PPG-1 Trideceth-6 | 1.50 | 1.50 | 1.50 | 1.50 | 1.50 | 1.50 |
| Cyclopentasiloxane | 4.00 | 4.00 | 4.00 | 4.00 | 4.00 | 4.00 |
| PEG-12 Dimethicone | 2.00 | 2.00 | 2.00 | 2.00 | 2.00 | 2.00 |
| Tocopheryl Acetate | 0.45 | 0.45 | 0.45 | 0.45 | 0.45 | 0.45 |
| Water (and) Citric Acid | Qs | Qs | Qs | Qs | Qs | Qs |
| Fragrance | Qs | Qs | Qs | Qs | Qs | Qs |

EXAMPLE 9

UV-A/UV-B Daily Care UV Protection Lotion

| INCI-Name | % w/w (as supplied) | | | | | |
|---|---|---|---|---|---|---|
| | 9a | 9b | 9c | 9d | 9e | 9f |
| Oleth-3 Phosphate | 0.60 | 0.60 | 0.60 | 0.60 | 0.60 | 0.60 |
| Steareth-21 | 2.50 | 2.50 | 2.50 | 2.50 | 2.50 | 2.50 |
| Steareth-2 | 1.00 | 1.00 | 1.00 | 1.00 | 1.00 | 1.00 |
| Cetyl Alcohol | 0.80 | 0.80 | 0.80 | 0.80 | 0.80 | 0.80 |
| Stearyl Alcohol | 1.50 | 1.50 | 1.50 | 1.50 | 1.50 | 1.50 |
| Tribehenin | 0.80 | 0.80 | 0.80 | 0.80 | 0.80 | 0.80 |
| Isohexadecane | 8.00 | 8.00 | 8.00 | 8.00 | 8.00 | 8.00 |
| Ethylhexyl Methoxycinnamate | 3.00 | 3.00 | 3.00 | 3.00 | 3.00 | 3.00 |
| Water | qs to 100 | qs to 100 | qs to 100 | qs to 100 | qs to 100 | qs to 100 |
| Glycerin | 2.00 | 2.00 | 2.00 | 2.00 | 2.00 | 2.00 |
| UV-absorber dispersion as described in example 5; compound of formula (101) | | 3.00 | | 11.00 | 2.00 | 6.00 |
| UV-absorber dispersion as described in example 3; compound of formula (101) | 3.00 | | 3.00 | | 3.00 | |
| Ubiquinone | 0.01 | 0.01 | 0.01 | 0.01 | 0.01 | 0.01 |
| Compound of the formula (u2) | 2.00 | | 1.10 | 1.10 | | |

EXAMPLE 9-continued

UV-A/UV-B Daily Care UV Protection Lotion

| INCI-Name | % w/w (as supplied) | | | | | |
|---|---|---|---|---|---|---|
| | 9a | 9b | 9c | 9d | 9e | 9f |
| Compound of the formula (v2) | | 1.30 | 1.10 | | | 1.10 |
| Compound of the formula (x2) | | | 1.50 | | 1.10 | |
| Compound of the formula (s2) | | | 1.10 | 2.00 | | |
| Compound of the formula (q2) | 1.10 | | 1.10 | | 1.50 | |
| Compound of the formula (b4) | | 1.10 | 1.10 | | | 2.00 |
| Micropigment dispersion of 2,4,6-Tris(p-biphenylyl)-s-triazine [CAS No. 31274-51-8] | 4.00 | 4.00 | 4.00 | 4.00 | 4.00 | 4.00 |
| Octocrylene | 4.00 | 4.00 | 4.00 | 4.00 | 4.00 | 4.00 |
| Avobenzone | 1.00 | 4.00 | 5.00 | 2.00 | 1.00 | 0.50 |
| Disodium EDTA | 0.10 | 0.10 | 0.10 | 0.10 | 0.10 | 0.10 |
| Water | 20.00 | 20.00 | 20.00 | 20.00 | 20.00 | 20.00 |
| Diazolidinyl Urea (and) Iodopropynyl Butylcarbamate | 0.15 | 0.15 | 0.15 | 0.15 | 0.15 | 0.15 |
| Propylene Glycol | 4.00 | 4.00 | 4.00 | 4.00 | 4.00 | 4.00 |
| Sodium Acrylates Copolymer (and) Paraffinium Liquidum (and) PPG-1 Trideceth-6 | 1.50 | 1.50 | 1.50 | 1.50 | 1.50 | 1.50 |
| Cyclopentasiloxane | 4.00 | 4.00 | 4.00 | 4.00 | 4.00 | 4.00 |
| PEG-12 Dimethicone | 2.00 | 2.00 | 2.00 | 2.00 | 2.00 | 2.00 |
| Tocopheryl Acetate | 0.45 | 0.45 | 0.45 | 0.45 | 0.45 | 0.45 |
| Water (and) Citric Acid | Qs | Qs | Qs | Qs | Qs | Qs |
| Fragrance | Qs | Qs | Qs | Qs | Qs | Qs |

EXAMPLE 10

UV-A/UV-B Daily Care UV Protection Lotion

| INCI-Name | % w/w (as supplied) | | | | | |
|---|---|---|---|---|---|---|
| | 10a | 10b | 10c | 10d | 10e | 10f |
| Oleth-3 Phosphate | 0.60 | 0.60 | 0.60 | 0.60 | 0.60 | 0.60 |
| Steareth-21 | 2.50 | 2.50 | 2.50 | 2.50 | 2.50 | 2.50 |
| Steareth-2 | 1.00 | 1.00 | 1.00 | 1.00 | 1.00 | 1.00 |
| Cetyl Alcohol | 0.80 | 0.80 | 0.80 | 0.80 | 0.80 | 0.80 |
| Stearyl Alcohol | 1.50 | 1.50 | 1.50 | 1.50 | 1.50 | 1.50 |
| Tribehenin | 0.80 | 0.80 | 0.80 | 0.80 | 0.80 | 0.80 |
| Isohexadecane | 8.00 | 8.00 | 8.00 | 8.00 | 8.00 | 8.00 |
| Ethylhexyl Methoxycinnamate | 3.00 | 3.00 | 3.00 | 3.00 | 3.00 | 3.00 |
| Water | qs to 100 | qs to 100 | qs to 100 | qs to 100 | qs to 100 | qs to 100 |
| Glycerin | 2.00 | 2.00 | 2.00 | 2.00 | 2.00 | 2.00 |
| UV-absorber dispersion as described in example 5; compound of formula (101) | | 2.00 | | 6.00 | 3.00 | 8.00 |
| UV-absorber dispersion as described in example 3; compound of formula (101) | 1.00 | | 4.00 | | 3.00 | |
| Compound of the formula (s2) | | 1.50 | | | | |
| Ubiquinone | | | 0.01 | | 0.01 | |
| Micropigment dispersion of 2,4,6-Tris(p-biphenylyl)-s-triazine [CAS No. 31274-51-8] | 4.00 | 4.00 | 4.00 | 4.00 | 4.00 | 4.00 |
| Octocrylene | 4.00 | 4.00 | 4.00 | 4.00 | 4.00 | 4.00 |
| Octyl methoxy cinnamate | 4.00 | 4.00 | 4.00 | 4.00 | 4.00 | 4.00 |
| Phenylbenzimidazolsulfonic acid (Eusolex 232) | | | | | | 2.00 |
| Disodium EDTA | 0.10 | 0.10 | 0.10 | 0.10 | 0.10 | 0.10 |
| Water | 20.00 | 20.00 | 20.00 | 20.00 | 20.00 | 20.00 |
| Diazolidinyl Urea (and) Iodopropynyl Butylcarbamate | 0.15 | 0.15 | 0.15 | 0.15 | 0.15 | 0.15 |
| Propylene Glycol | 4.00 | 4.00 | 4.00 | 4.00 | 4.00 | 4.00 |
| Sodium Acrylates Copolymer (and) Paraffinium Liquidum (and) PPG-1 Trideceth-6 | 1.50 | 1.50 | 1.50 | 1.50 | 1.50 | 1.50 |
| Cyclopentasiloxane | 4.00 | 4.00 | 4.00 | 4.00 | 4.00 | 4.00 |

EXAMPLE 10-continued

UV-A/UV-B Daily Care UV Protection Lotion

| INCI-Name | % w/w (as supplied) | | | | | |
|---|---|---|---|---|---|---|
| | 10a | 10b | 10c | 10d | 10e | 10f |
| PEG-12 Dimethicone | 2.00 | 2.00 | 2.00 | 2.00 | 2.00 | 2.00 |
| Tocopheryl Acetate | 0.45 | 0.45 | 0.45 | 0.45 | 0.45 | 0.45 |
| Water (and) Citric Acid | Qs | Qs | Qs | Qs | Qs | Qs |
| Fragrance | Qs | Qs | Qs | Qs | Qs | Qs |

EXAMPLE 11

UV Day Lotion

| | INCI-Name | % w/w (as supplied) |
|---|---|---|
| Part A | Cetyl Phosphate | 1.75 |
| | C12-C15 Alkyl Benzoate | 4.00 |
| | Cetearyl Alcohol/PEG-20 Stearate | 2.00 |
| | Ethoxydiglycol Oleate | 2.00 |
| | Stearic Acid | 1.50 |
| | Ethylhexyl Methoxycinnamate | 3.00 |
| | Isononyl Isononanoate | 2.00 |
| | Bis-ethylhexyloxyphenol methoxyphenyl triazine (Tinosorb S) | 1.00 |
| Part B | Aqua | qs to 100 |
| | Xanthan Gum | 0.35 |
| | UV-absorber dispersion as described in example 3 | 5.00 |
| | Micropigment dispersion of 2,4,6-Tris(p-biphenylyl)-s-triazine [CAS No. 31274-51-8] | 2.00 |
| | Disodium EDTA | 0.20 |
| | Propylene Glycol | 2.00 |
| | Diazolidinyl Urea (and) Methylparaben (and) Propylparaben (and) Propylene Glycol | 0.70 |
| | Glycerin | 1.50 |
| Part C | Cyclopentasiloxane (and) Dimethiconol | 1.00 |
| | Ethoxydiglycol | 3.00 |
| | Dimethicone | 2.00 |
| Part D | Triethanolamine | qs |

Manufacturing Instruction:

Part A by is prepared by incorporating all ingredients, then stirred under moderate speed and heated to 75° C. Part B s prepared and heated to 75° C. At this temperature part B is poured into part A under progressive stirring speed. Then the mixture is homogenized (30 sec., 15000 rpm). At a temperature <55° C. the ingredients of part C are incorporated. The mixture is cooled down under moderate stirring, then the pH is checked and adjusted with triethanolamine.

EXAMPLE 12

Sun Protection Emulsion

| | INCI-Name | % w/w (as supplied) |
|---|---|---|
| Part A | Cetearyl Alcohol (and) Dicetyl Phosphate (and) Ceteth-10 Phosphate | 4.00 |
| | C12-15 Alkyl Benzoate | 2.00 |
| | Dicaprylyl Ether | 3.00 |
| | Ethoxydiglycol Oleate | 2.00 |
| | Zinc oxide (60 nm primary particle size) | 2.00 |
| | Titanium Dioxide (Eusolex T-2000) | 4.00 |
| | Stearic Acid | 1.00 |
| | Ethylhexyl Methoxycinnamate | 3.00 |
| | Sodium Acrylates Copolymer (and) Glycine Soja (and) PPG-1 Trideceth-6 | 0.30 |
| | Squalane | 3.50 |

EXAMPLE 12-continued

Sun Protection Emulsion

| | INCI-Name | % w/w (as supplied) |
|---|---|---|
| Part B | Aqua | qs to 100 |
| | UV-absorber dispersion as described in example 5 | 5.00 |
| | Micropigment dispersion of 2,4,6-Tris(p-biphenylyl)-s-triazine [CAS No. 31274-51-8] | 2.00 |
| Part C | Diazolidinyl Urea (and) Iodopropynyl Butylcarbamate | 0.15 |
| | Propylene Glycol | 2.50 |
| | Aqua | 10.00 |
| Part D | Cyclopentasiloxane, Dimethiconol | 2.00 |
| | Ethoxydiglycol | 5.00 |
| | Cyclopentasiloxane (and) Dimethicone/Vinyldimethicone Crosspolymer | 2.00 |
| Part E | Sodium Hydroxide | 0.10 |

Manufacturing Instruction:

Part A is prepared by incorporating all ingredients, then stirred under moderate speed and heated to 75° C. Part B is prepared and heated to 75° C. At this temperature, part B is poured into part A under progressive stirring speed. Below 65° C. the ingredients of part D are added separately. After cooling down under moderate stirring to 55° C. part C is added. The pH is then checked and adjusted with sodium hydroxide. The mixture is homogenized for 30 sec at 16000 rpm.

EXAMPLE 13

Every Day Lotion

| | INCI-Name | % w/w (as supplied) |
|---|---|---|
| Part A | Stearyl Phosphate | 5.00 |
| | Tricontanyl PVP | 1.00 |
| | Ethoxydiglycol Oleate | 3.00 |
| | Squalane | 5.00 |
| | C12-15 Alkyl Benzoate | 5.00 |
| | Ethylhexyl Methoxycinnamate | 3.00 |
| | Glyceryl Stearate | 2.00 |
| | Cetyl Alcohol | 2.00 |
| | Butyl methoxydibenzoylmethane (Parsol 1789) | 1.50 |
| Part B | Aqua | 20.00 |
| | UV-absorber dispersion as described in example 3 | 3.00 |
| | Micropigment dispersion of 2,4,6-Tris(p-biphenylyl)-s-triazine [CAS No. 31274-51-8] | 2.00 |
| | Methylene bis-benzotriazolyl tetramethyl-butylphenol (TinosorbM) | 2.00 |

EXAMPLE 13-continued

Every Day Lotion

| | INCI-Name | % w/w (as supplied) |
|---|---|---|
| Part C | Aqua | qs to 100 |
| | Steareth-10 Allyl Ether/Acrylates Copolymer | 0.50 |
| | Glycerin | 2.50 |
| | Diazolidinyl Urea (and) Iodopropynyl Butylcarbamate | 0.15 |
| | Sodium Lauroyl Glutamate | 0.70 |
| Part D | Cyclopentasiloxane (and) Dimethiconol | 1.50 |
| | Triethanolamine | 1.85 |

Manufacturing Instruction:

Part A is prepared by incorporating all ingredients, then stirred under moderate speed and heated to 75° C. Part C is prepared and heated to 75° C. Part C is poured into the part A under moderate stirring. Immediately after the emulsification part B is added, then neutralized with a part of the triethanolamine. The mixture is homogenized for 30 sec. After cooling down under moderate stirring Cyclopentasiloxane (and) Dimethiconol are added. Below 35° C. the pH is checked and adjusted with triethanolamine.

EXAMPLE 14

Sprayable Sunscreen Emulsion

| | INCI-Name | % w/w (as supplied) |
|---|---|---|
| Part A | Ceteareth-15 (and) Glyceryl Stearate | 3.00 |
| | Stearyl Alcohol | 1.00 |
| | Cetyl Ricinoleate | 0.80 |
| | Dicaprylyl Ether | 3.00 |
| | C12-15 Alkyl Benzoate | 3.00 |
| | Isohexadecane | 2.50 |
| | Stearyl Dimethicone | 1.00 |
| | Ethylhexyl Methoxycinnamate | 4.00 |
| | Cetyl Alcohol | 0.80 |
| | Di-C12-13 Alkyl Tartrate | 3.00 |
| Part B | Aqua | qs to 100 |
| | Steareth-10 Allyl Ether/Acrylates Copolymer | 0.45 |
| | PEG-7 Glyceryl Cocoate | 2.50 |
| | Glycerin | 2.00 |
| | Propylene Glycol | 3.00 |
| Part C | Diazolidinyl Urea (and) Iodopropynyl Butylcarbamate | 0.15 |
| | Aqua | 20.00 |
| | Micropigment dispersion of 2,4,6-Tris(p-biphenylyl)-s-triazine [CAS No. 31274-51-8] | 2.00 |
| | UV-absorber dispersion as described in example 3 | 12.00 |
| | Titanium Dioxide (Eusolex T-2000) | 8.00 |
| Part D | Cyclopentasiloxane (and) Dimethiconol | 0.85 |
| Part E | Sodium Hydroxide (and) Water | qs to pH 6.50-7.00 |
| Part F | Fragrance | qs |

Manufacturing Instruction

Part A and part B are heated up to 80° C. Part A is blended into part B under stirring and homogenized with an UltraTurrax at 11000 rpm for 30 sec. Part C is heated to 60° C. and added slowly to the emulsion. After cooling down to 40° C. part D is incorporated at room temperature and part E is added.

EXAMPLE 15

Daily Care Lotion

| | INCI-Name | % w/w (as supplied) |
|---|---|---|
| Part A | Polyglyceryl Methyl Glucose Distearate | 2.50 |
| | Cetearyl Alcohol | 2.00 |
| | Octyl Stearate | 3.00 |
| | Caprylic/Capric Triglyceride | 4.00 |
| | Isohexadecane | 4.00 |
| | Ethylhexyl Methoxycinnamate | 2.70 |
| Part B | Aqua | qs ad 100 |
| | Glycerin | 5.00 |
| | Phenoxyethanol (and) Methylparaben (and) Butylparaben (and) Ethylparaben (and) Propylparaben | 0.50 |
| | Micropigment dispersion of 2,4,6-Tris(p-biphenylyl)-s-triazine [CAS No. 31274-51-8] | 2.00 |
| | UV-absorber dispersion as described in example 5 | 8.00 |
| Part C | Cyclomethicone (and) Dimethicone | 3.00 |
| Part D | Steareth-10 Allyl Ether/Acrylates Copolymer | 0.50 |

Manufacturing Instruction

Part A and B are heated to 75° C. Part A is added into part B under continuous stirring and homogenized with 11000 rpm for 1 minute. After cooling down to 50° C. part C is added under continuous stirring. After cooling further down to 30° C. part D is added. Afterwards the pH is adjusted between 6.00-6.50.

EXAMPLE 16

Daily Care with UV Protection

| | INCI-Name | % w/w (as supplied) |
|---|---|---|
| Part A | Glyceryl Stearate SE | 3.00 |
| | Glyceryl Stearate and PEG-100 Stearate | 3.50 |
| | Cetyl Alcohol | 1.50 |
| | Myristyl Myristate | 2.00 |
| | Isopropyl Palmitate | 2.50 |
| | Paraffinum Perliquidum | 5.00 |
| | Octyl Dimethyl PABA | 3.00 |
| Part B | Aqua | qs to 100 |
| | Propylene Glycol | 7.50 |
| | Phenoxyethanol (and) Methylparaben (and) Butylparaben (and) Ethylparaben (and) Propylparaben | 1.00 |
| Part C | Aqua | 30.00 |
| | Micropigment dispersion of 2,4,6-Tris(p-biphenylyl)-s-triazine [CAS No. 31274-51-8] | 2.00 |
| | UV-absorber dispersion as described in example 5 | 10.00 |
| Part D | Sodium Acrylates Copolymer (and) Paraffinium Liquidum (and) PPG-1 Trideceth-6 | 2.00 |
| Part E | Citric Acid | 0.30 |

Manufacturing Instruction:

Part A and B are heated separately to 75° C. After adding part B into part A the mixture is homogenized with Ultra Turrax for one minute at 11000 rpm. After cooling down to 50° C. part C is added. Afterwards the mixture is homogenized for one minute at 16000 rpm. At a temperature<40° C. part D is added. At room temperature the pH-value is adjusted with part E between 6.00 and 6.50.

EXAMPLE 17

O/W Every Day UV Protection Lotion

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | C12-15 Alkyl Benzoate | 5.00 |
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | Micropigment dispersion of 2,4,6-Tris(p-biphenylyl)-s-triazine [CAS No. 31274-51-8] | 2.00 |
| | UV-absorber dispersion as described in example 3 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11000 rpm and part C is incorporated. After cooling down to 40° C. part D is added. At room temperature the pH-value is adjusted with Sodium Hydroxide between 6.30 and 6.70 and part F is added.

EXAMPLE 18

O/W Every Day UV Protection

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | C12-15 Alkyl Benzoate | 4.00 |
| | Isopropyl Palmitate | 4.00 |
| | Ethylhexyl Methoxycinnamate | 3.00 |
| | Benzophenone-3 | 1.00 |
| | Benzophenone-4 | 1.00 |
| Part B | Water | qs to 100 |
| | Polysorbate 60 | 0.50 |
| | Glycerin | 3.00 |
| Part C | Water | 10.00 |
| | Micropigment dispersion of 2,4,6-Tris(p-biphenylyl)-s-triazine [CAS No. 31274-51-8] | 2.00 |
| | UV-absorber dispersion as described in example 3 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11000 rpm and part C is incorporated. After cooling down to 40° C. part D is added. At room temperature the pH-value is adjusted with Sodium Hydroxide between 6.30 and 6.70 and part F is added.

EXAMPLE 19

Sunscreen Cream

| | INCI-Name | % w/w (as supplied) |
|---|---|---|
| Part A | Cetearyl Alcohol (and) Dicetyl Phosphate (and) Ceteth-10 Phosphate | 4.50 |
| | C12-15 Alkyl Benzoate | 6.00 |
| | Caprylic/Capric Triglyceride | 7.00 |
| | Pentaerythritol Tetraisostearate | 2.00 |
| | Ethylhexyl Methoxycinnamate | 3.00 |
| | Isoamyl p-Methoxycinnamate | 2.00 |
| Part B | Aqua | qs to 100 |
| | Glycerin | 2.00 |
| | Propylene Glycol | 1.50 |
| | Magnesium Aluminium Silicate | 1.20 |
| Part C | Steareth-10 Allyl Ether/Acrylates Copolymer | 0.50 |
| | Micropigment dispersion of 2,4,6-Tris(p-biphenylyl)-s-triazine [CAS No. 31274-51-8] | 4.00 |
| | UV-absorber dispersion as described in example 5 | 12.00 |
| Part D | Phenyl Trimethicone | 1.50 |
| | Phenoxyethanol (and) Methylparaben (and) Butylparaben (and) Ethylparaben (and) Propylparaben | 0.70 |
| Part E | Sodium Hydroxide | 0.90 |

Manufacturing Instruction:

Part A and part B are heated separately to 75° C. Part B is added into part A under continuous stirring and afterwards homogenized with Ultra Turrax for 30 sec at 11000 rpm. After cooling down to 60° C. part C is added. At 40° C. part C is added and homogenized for 15 sec at 11000 rpm. At room temperature the pH-value is adjusted with part E.

EXAMPLE 20

UVA/UVB Daily Care Lotion, type O/W

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Mineral Oil | 15.00 |
| Part B | Water | qs to 100 |
| | Polysorbate 60 | 0.50 |
| | Glycerin | 3.00 |
| Part C | Water | 10.00 |
| | Micropigment dispersion of 2,4,6-Tris(p-biphenylyl)-s-triazine [CAS No. 31274-51-8] | 8.00 |
| | UV-absorber dispersion as described in example 5 | 8.00 |
| Part D | Steareth-10 Allyl Ether/Acrylates Copolymer | 1.50 |
| | Phenoxyethanol (and) Methylparaben (and) Ethylparaben (and) Butylparaben (and) Propylparaben (and) Isobutylparaben | 0.70 |
| Part E | Water (and) Sodium Hydroxide | qs |
| Part F | Fragrance | qs |

Manufacturing Instruction:

Part A and B are heated separately to 75° C.; part C to 60° C. Part B is poured into part A under stirring. After one-minute of homogenization at 11000 rpm part C is added to the mixture of A/B. After cooling down to 40° C. part D is incorporated. At room temperature the pH value is adjusted with part E between 6.3 and 7.0. Finally part F is added.

EXAMPLE 21

UVA/UVB Daily Care Lotion, type O/W

| | INCI-Name | % w/w (as supplied) |
|---|---|---|
| Part A | Oleth-3 Phosphate | 0.60 |
| | Steareth-21 | 2.50 |
| | Steareth-2 | 1.00 |
| | Cetyl Alcohol | 0.80 |
| | Stearyl Alcohol | 1.50 |
| | Tribehenin | 0.80 |
| | Isohexadecane | 8.00 |
| Part B | Water | qs to 100 |
| | Glycerin | 2.00 |
| | Disodium EDTA | 0.10 |
| Part C | Cyclopentasiloxane | 4.50 |
| | PEG-12 Dimethicone | 2.00 |
| Part D | Sodium Acrylates Copolymer (and) Mineral Oil (and) PPG-1 Trideceth-6 | 1.50 |
| Part E | UV-absorber dispersion as described in example 3 | 10.00 |
| | Micropigment dispersion of 2,4,6-Tris(p-biphenylyl)-s-triazine [CAS No. 31274-51-8] | 10.00 |
| Part F | Tocopheryl Acetate | 0.45 |
| | DMDM Hydantoin (and) Iodopropynyl Butylcarbamate (and) Aqua (and) Butylene Glycol | 0.85 |
| Part G | Water (and) Citric Acid | qs |
| | Fragrance | qs |

Manufacturing Instruction:

Part A and part B are heated separately to 75° C. Part A is poured into part B under stirring. Immediately after the emulsification, part C is added to the mixture and homogenized with an Ultra Turrax at 11000 rpm for 30 sec. After cooling down to 65° C. Sodium Acrylates Copolymer (and) Mineral Oil (and) PPG-1 Trideceth-6 At 50° C. is added slowly to the UV absorber dispersion. At about 35-30° C. part F is incorporated. The pH is adjusted with part G between 5.5 and 6.5.

EXAMPLE 22

UV-A/UV-B Every Day Protection Lotion O/W

| | INCI-Name | % w/w (as supplied) |
|---|---|---|
| Part A | Glyceryl Dilaurate | 2.00 |
| | Ethylhexyl Palmitate | 6.00 |
| | Cetyl Alcohol | 1.00 |
| | Glyceryl Stearate | 2.00 |
| | Laureth-23 | 1.00 |
| | Isopropyl Palmitate | 2.00 |
| | Tribehenin | 0.80 |
| | Beeswax | 1.50 |
| | Lanolin Oil | 1.00 |
| Part B | Water | qs to 100 |
| | Propylene Glycol | 4.00 |
| | Water (and) Titanium Dioxide (10-20 nm primary particle size) (and) Alumina (and) Sodium Metaphosphate (and) Phenoxyethanol (and) Sodium Methylparaben | 4.00 |
| Part C | Steareth-10 Allyl Ether/Acrylates Copolymer | 1.00 |
| Part D | Phenoxyethanol (and) Methylparaben (and) Ethylparaben (and) Butylparaben (and) Propylparaben (and) Isobutylparaben | 1.00 |
| | Micropigment dispersion of 2,4,6-Tris(p-biphenylyl)-s-triazine [CAS No. 31274-51-8] | 5.00 |
| | UV-absorber dispersion as described in example 5 | 8.00 |
| Part E | Water (and) Sodium Hydroxide | qs |

Manufacturing Instruction:

Part A and part B are heated separately up to 80° C. Part A is poured into part B while stirring and homogenized with an Ultra Turrax by 11000 rpm for 30 sec. After cooling down to 60° C. part C is incorporated. At 40° C. part D is added slowly under continuous stirring. The pH is adjusted with part E between 6.50-7.00.

EXAMPLE 23

Sprayable Sunscreen Lotion

| | INCI-Name | % w/w (as supplied) |
|---|---|---|
| Part A | Potassium Cetyl Phosphate | 0.20 |
| | Isohexadecane | 7.00 |
| | VP/Eicosene Copolymer | 1.50 |
| | Di-C12-13 Alkyl Tartrate | 6.00 |
| | Ethylhexyl Triazone | 2.50 |
| | C12-15 Alkyl Benzoate | 4.50 |
| Part B | Water | qs to 100 |
| | Sorbeth-30 | 2.00 |
| | Sorbitan Stearate (and) Sucrose Cocoate | 4.00 |
| | Titanium Dioxide (and) Alumina (and) Silica (and) Sodium Polyacrylate | 2.50 |
| Part C | Water | 30.00 |
| | Micropigment dispersion of 2,4,6-Tris(p-biphenylyl)-s-triazine [CAS No. 31274-51-8] | 3.00 |
| | UV-absorber dispersion as described in example 3 | 12.00 |
| Part D | Phenoxyethanol (and) Methylparaben (and) Ethylparaben (and) Butylparaben (and) Propylparaben (and) Isobutylparaben | 0.70 |
| Part E | Water (and) Citric Acid | qs |

Manufacturing Instruction:

Part A and part B are heated separately up to 80° C., part C is heated to 50° C. Part B is poured into part A and homogenized with an Ultra Turrax for 1 minute at 11000 rpm. After cooling down to 50° C. part C is added under continuous stirring. At 40° C. part D is incorporated and homogenized again for 10 sec. at 11000 rpm. The pH is adjusted with part E.

EXAMPLE 24

O/W Every Day UV Protection Lotion

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | Caprylic/Capric Triglyceride | 5.00 |
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | UV-absorber dispersion as described in example 5 | 8.00 |
| | Micropigment dispersion of 2,4,6-Tris(p-biphenylyl)-s-triazine [CAS No. 31274-51-8] | 2.00 |
| | ZnO (Nanox Zinc Oxide) | 3.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and part B are heated separately up to 75° C., part C is heated to 60° C. Afterwards part B is poured into part A under stirring. The mixture is homogenized with an Ultra Turrax for 30 sec. at 11 000 rpm and part C is incorporated. After cooling down to 40° C. part D is added. At room temperature the pH-value is adjusted with Sodium Hydroxide between 6.30 and 6.70 and part F is added.

EXAMPLE 25

Water resistant Sunscreen Emulsion

| | INCI-Name | % w/w (as supplied) |
|---|---|---|
| Part A | Polyglyceryl-10 Pentastearate (and) Behenyl Alcohol (and) Sodium Stearoyl Lactylate | 2.50 |
| | VP/Eicosene Copolymer | 1.50 |
| | Stearyl Alcohol | 1.50 |
| | Squalane | 4.00 |
| | C12-15 Alkyl Benzoate | 5.50 |
| | Octocrylene | 1.50 |
| | 4-Methylbenzylidene Camphor | 3.00 |
| | Ethylhexyl Methoxycinnamate | 2.00 |
| | Ethyl hexyl salicylate (Neoheliopan OS) | 2.00 |
| Part B | Water | qs to 100 |
| | Glycerin | 1.80 |
| | Steareth-10 Allyl Ether/Acrylates Copolymer | 0.80 |
| Part C | UV-absorber dispersion as described in example 3 | 9.00 |
| | Micropigment dispersion of 2,4,6-Tris(p-biphenylyl)-s-triazine [CAS No. 31274-51-8] | 2.00 |
| Part D | VP/Hexadecene Copolymer | 2.70 |
| | Cyclomethicone | 1.50 |
| | Phenoxyethanol (and) Methylparaben (and) Ethylparaben (and) Butylparaben (and) Propylparaben (and) Isobutylparaben | 0.70 |
| Part E | Aqua (and) Tocopheryl Acetate (and) Caprylic/Capric Triglyceride (and) Polysorbate 80 (and) Lecithin | 3.50 |
| Part F | Fragrance | qs |
| | Water (and) Sodium Hydroxide | qs |

Manufacturing Instruction:

Part A and part B are heated separately to 80° C. Part A is poured into part B under continuous stirring. Afterwards the mixture is homogenized with an Ultra Turrax at 11000 rpm for 1 min. After cooling down to 60° C. part C is incorporated. At 40° C. part D is added and the mixture homogenized for a short time again. At 35° C. part E is added and at room temperature Fragrance is added. Finally the pH is adjusted with Sodium Hydroxide.

EXAMPLE 26

UVA/UVB Sun Protection Lotion, O/W type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| | 2,2'-bis(1,4-phenylene)-1H-benzimidazole-4,6-disulphonic acid mono sodium salt (Neoheliopan AP) | 2.00 |
| Part C | Steareth-10 Allyl Ether/Acrylates Copolymer | 0.50 |

EXAMPLE 26-continued

UVA/UVB Sun Protection Lotion, O/W type

| | INCI-Name | % w/w (as supplied) |
|---|---|---|
| Part D | UV-absorber dispersion as described in example 5 | 8.00 |
| | Micropigment dispersion of 2,4,6-Tris(p-biphenylyl)-s-triazine [CAS No. 31274-51-8] | 2.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under mode-rate stirring. The mixture is homogenized with an Ultra Turrax at 11000 rpm for 1 minute. After cooling down to 70° C. part C is added under stirring. After cooling further down to 50° C. part D is incorporated very slowly. At 40° C. part E is added. At room temperature the pH adjusted with part F to 7.00 and part G is added.

EXAMPLE 27

UVA/UVB Sun Protection Lotion, O/W type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 4.00 |
| | Diethylhexyl butamido triazone (UVASORB HEB) | 1.00 |
| Part B | Water | qs to 100 |
| | Glycerin | 3.00 |
| Part C | Steareth-10 Allyl Ether/Acrylates Copolymer | 0.50 |
| | Micropigment dispersion of 2,4,6-Tris(p-biphenylyl)-s-triazine [CAS No. 31274-51-8] | 2.00 |
| Part D | UV-absorber dispersion as described in example 3 | 20.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for 1 minute. After cooling down to 70° C. add part C is added under stirring. After cooling further down to 50° C. part D is incorporated very slowly. At 40° C. part E is added. At room temperature the pH is adjusted with part F to 7.00 and part G is added.

EXAMPLE 28

Sunscreen Lotion

| | INCI-Name | % w/w (as supplied) |
|---|---|---|
| Part A | Cetearyl Alcohol (and) Dicetyl Phosphate (and) Ceteth-10 Phosphate | 4.00 |
| | C12-15 Alkyl Benzoate | 2.00 |
| | Dicaprylyl Ether | 3.00 |
| | Ethoxydiglycol Oleate | 2.00 |
| | Stearic Acid | 1.00 |
| | Ethylhexyl Methoxycinnamate | 2.00 |
| | Sodium Acrylates Copolymer (and) Glycine Soja (and) PPG-1 Trideceth-6 | 0.30 |
| | Squalane | 3.50 |
| | VP/Eicosene Copolymer | 2.00 |
| | Benzylidene malonate polysiloxane (Parsol SLX) | 2.00 |
| Part B | Water | qs to 100 |
| | Micropigment dispersion of 2,4,6-Tris(p-biphenylyl)-s-triazine [CAS No. 31274-51-8] | 2.00 |
| | UV-absorber dispersion as described in example 3 | 5.00 |
| Part C | Diazolidinyl Urea (and) Iodopropynyl Butylcarbamate | 0.15 |
| | Propylene Glycol | 2.50 |
| | Water | 10.00 |
| Part D | Cyclopentasiloxane (and) Dimethiconol | 2.00 |
| | Ethoxydiglycol | 5.00 |
| | Cyclopentasiloxane (and) Dimethicone/Vinyl Dimethicone Crosspolymer | 2.00 |
| Part E | Aqua (and) Sodium Hydroxide | qs |
| Part F | Fragrance | qs |

Manufacturing Instruction

Part A and part B are heated separately up to 75° C. Part B is poured into part A under progressive stirring speed. At a temperature <65° C. the ingredients of part D are added separately. After cooling down to 55° C. under moderate stirring part C is added. At a temperature <35° C. the pH is checked and adjusted with Sodium Hydroxide and homogenized with an Ultra Turrax for 30 sec. at 11000 rpm. At room temperature part F is added.

EXAMPLE 29

W/O Sunscreen Lotion

| | INCI-Name | % w/w (as supplied) |
|---|---|---|
| Part A | PEG-7 Hydrogenated Castor Oil | 3.00 |
| | Polyglyceryl-3 Diisostearate | 4.00 |
| | Microcrystalline Wax | 1.00 |
| | Magnesium Stearate | 1.50 |
| | Propylparaben | 0.10 |
| | Mineral Oil | 15.00 |
| | Octyldodecanol | 8.00 |
| | Ethylhexyl Triazone | 1.00 |
| | Ethylhexyl Methoxycinnamate | 2.00 |
| | Diethylamino Hydroxybenzoyl Hexyl Benzoate (Uvinul A+) | 1.50 |
| Part B | Water | qs to 100 |
| | Water (and) Citric Acid | 0.05 |
| | Methylparaben | 0.15 |
| | Magnesium Sulfate | 0.50 |
| Part C | UV-absorber dispersion as described in example 5 | 9.00 |
| | Micropigment dispersion of 2,4,6-Tris(p-biphenylyl)-s-triazine [CAS No. 31274-51-8] | 2.00 |
| | Fragrance | qs |

Manufacturing Instruction:

Part A is heated to 80° C. whilst stirring. Part B is added into part A and homogenized with an Ultra Turrax at 11000 rpm for one minute. After cooling down to 30° C. part C is incorporated.

EXAMPLE 30

Skin Protection Sunscreen Lotion W/O

| | INCI-Name | % w/w (as supplied) |
|---|---|---|
| Part A | Polyglyceryl-2 Dipolyhydroxystearate | 3.00 |
| | Glyceryl Oleate | 3.00 |
| | Cetearyl Isononanoate | 7.00 |
| | Hexyl Laurate | 6.00 |
| | Dicaprylyl Ether | 6.00 |
| | Propylparaben | 0.10 |
| | Hexyldecanol | 3.00 |
| | Magnesium Stearate | 1.00 |
| | Beeswax | 1.00 |
| | Ethylhexyl Methoxycinnamate | 4.00 |
| Part B | Water | qs to 100 |
| | Methylparaben | 0.15 |
| | Magnesium Sulfate | 1.00 |
| | Micropigment dispersion of 2,4,6-Tris(p-biphenylyl)-s-triazine [CAS No. 31274-51-8] | 2.00 |
| Part C | UV-absorber dispersion as described in example 3 | 6.00 |

Manufacturing Instruction:

Part A is heated separately to 80° C. under gentle stirring. Part B is added to part A and homogenized for one minute at 11000 rpm. After cooling down to 30° C. part C is added under continuous stirring.

EXAMPLE 31

Sunscreen

| | INCI-Name | % w/w (as supplied) |
|---|---|---|
| Part A | Hexyldecanol | 2.70 |
| | Polyoxyethylen-2-stearylalkohol | 2.20 |
| | PEG-30 Dipolyhydroxystearate | 1.10 |
| | UV-absorber as described in example 3; pH = 7 adjusted with citric acid | 6 |
| | Micropigment dispersion of 2,4,6-Tris(p-biphenylyl)-s-triazine [CAS No. 31274-51-8] | 2.00 |
| Part B | Cetyl Ethylhexanoate | 4.00 |
| | Isohexadecane | 4.00 |
| | Ethxlhexyl methoxy cinnamate | 0.00 |
| | Bis-ethylhexyloxyphenol methoxyphenyl triazine (Tinosorb S) | 0.00 |
| | Phenoxyethanol (and) Methylparaben (and) Ethylparaben (and) Butylparaben (and) Propylparaben (and) Isobutylparaben | 0.60 |
| Part C | Water | Qs. 100 |
| | Glycerin | 3.00 |
| Part D | Sodium Acrylates Copolymer (and) Mineral Oil (and) PPG-1 Trideceth-6 | 2.00 |
| Part E | Cyclopentasiloxane | 2.00 |

This Sunscreen may also be used as an anti-wrinkle perception modifier.

Manufacturing Instruction

Mix part A and heat up to 60° C. to 65° C. and add Disp. Slowly under fast stirring Add part B under moderate stirring at 60° C.

Add part B into part A under stirring at 60° C.-75° C.

Add part C under stirring until homogenization (emulsification at fast stirring, may be with ultra turrax)

Add part D under moderate stirring (60° C.)

Finally add part E under stirring (60° C.) and cool down under moderate stirring

EXAMPLE 32

PEG-free sunscreen

| | INCI-Name | % w/w (as supplied %) |
|---|---|---|
| Part A | Hexyldecanol | 2.30 |
| | Polyglyceryl-3 Methylglucose Distearate | 1.40 |
| | Polyglyceryl polyhydroxy stearate | 1.40 |
| | UV-absorber as described in example 5; pH = 7 adjusted with citric acid | 5.00 |
| | Micropigment dispersion of 2,4,6-Tris(p-biphenylyl)-s-triazine [CAS No. 31274-51-8] | 2.00 |
| Part B | Cetyl Ethylhexanoate | 3.00 |
| | Isohexadecane | 3.00 |
| | Ethylhexyl methoxy cinnamate | 3.00 |
| | Bis-ethylhexyloxyphenol methoxyphenyl triazine (Tinosorb S) | 2.00 |
| | Phenoxyethanol (and) Methylparaben (and) Ethylparaben (and) Butylparaben (and) Propylparaben (and) Isobutylparaben | 0.60 |
| Part C | Water | Qs 100 |
| | Glycerin | 3.00 |
| Part D | Sodium Acrylates Copolymer (and) Mineral Oil (and) PPG-1 Trideceth-6 | 1.50 |
| Part E | Cyclopentasiloxane | 1.50 |

The invention claimed is:

1. A method of reducing browning and aging of the skin, wherein said method comprises applying to said skin an effective amount of an aqueous dispersion comprising a) a micronized sparingly soluble organic compound which has a UV-Vis spectrum with a maximum from 380 to 420 nm selected from the compound of formula (2)

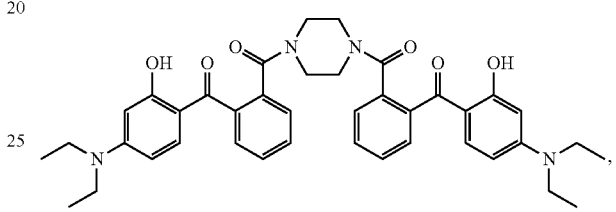

(2)

wherein the crystalline form is characterized by an X-ray diffraction pattern and obtained using Cu-Ka radiation which exhibits diffraction angels (2Θ) as seen below:

| 2-Theta Scale | Lin [Cps] | 2-Theta Scale | Lin [Cps] | 2-Theta Scale | Lin [Cps] |
|---|---|---|---|---|---|
| 8.5 | 2080 | 15.3 | 420 | 20.8 | 950 |
| 10.5 | 1450 | 11.8 | 2050 | 22.8 | 530 |
| 12.7 | 400 | 18.0 | 350 | 25.7 | 600 |
| 13.8 | 430 | 19.8 | 1350 | 30.7 | 300 |
| 14.5 | 940 | | | | | and b) a dispersing agent selected from anionic, non-ionic and amphoteric surfactants.

2. A method according to claim 1 wherein the micronized sparingly soluble organic compound (2) is used together in combination with further UV absorbers.

3. A crystalline form of the compound of formula (2)

wherein the crystalline form is characterized by an X-ray diffraction pattern and obtained using Cu-Ka-radiation which exhibits diffraction angles (2Θ)as seen below:

| 2-Theta Scale | Lin [Cps] |
|---|---|
| 8.5 | 2080 |
| 10.5 | 1450 |
| 12.7 | 400 |
| 13.8 | 430 |
| 14.5 | 940 |
| 15.3 | 420 |
| 11.8 | 2050 |
| 18.0 | 350 |
| 19.8 | 1350 |
| 20.8 | 950 |
| 22.8 | 530 |
| 25.7 | 600 |
| 30.7 | 300. |

* * * * *